US012752257B2

(12) United States Patent
Tango et al.

(10) Patent No.: US 12,752,257 B2
(45) Date of Patent: Oct. 6, 2026

(54) ALUMINA SUPPORT

(71) Applicant: KANEKA CORPORATION, Osaka (JP)

(72) Inventors: Takeru Tango, Tokyo (JP); Tetsunori Yoshioka, Osaka (JP)

(73) Assignee: KANEKA CORPORATION, Osaka (JP)

( * ) Notice: Subject to any disclaimer, the term of this patent is extended or adjusted under 35 U.S.C. 154(b) by 750 days.

(21) Appl. No.: 18/106,068

(22) Filed: Feb. 6, 2023

(65) Prior Publication Data

US 2023/0173460 A1 Jun. 8, 2023

Related U.S. Application Data

(63) Continuation of application No. PCT/JP2021/028855, filed on Aug. 3, 2021.

(30) Foreign Application Priority Data

Aug. 6, 2020 (JP) ................................ 2020-134207

(51) Int. Cl.

*C07C 17/156* (2006.01)
*B01J 21/04* (2006.01)
(Continued)

(52) U.S. Cl.

CPC ............ *B01J 21/04* (2013.01); *B01J 35/615* (2024.01); *B01J 35/633* (2024.01); *B01J 35/647* (2024.01);
(Continued)

(58) Field of Classification Search

CPC . B01J 21/04; B01J 35/55; B01J 35/615; B01J 35/66; C07C 17/156
See application file for complete search history.

(56) References Cited

U.S. PATENT DOCUMENTS 4,081,406 A * 3/1978 Sawyer .................. B01J 23/882
502/259
4,366,093 A 12/1982 Shiozaki et al.
(Continued)

FOREIGN PATENT DOCUMENTS

JP 656-141842 A 11/1981
JP H4-227065 A 8/1992
(Continued)

OTHER PUBLICATIONS

Machine translation of JP2012166959, Sep. 6, 2012.*

*Primary Examiner* — Jun Li

(74) *Attorney, Agent, or Firm* — Osha Bergman Watanabe & Burton LLP

(57) ABSTRACT

An alumina support for a catalyst for a gas-phase reaction that increases the catalytic activity and allows a reduction in by-product yield, and a catalyst for a gas-phase reaction that is a metal compound supported on the alumina support are provided. The alumina support for a catalyst for a gas-phase reaction has a tubular shape with at least one hollow through hole and a BET specific surface area of 140 to 280 $m^2/g$. In this alumina support, a volume (total pore volume) of pores with a diameter of not less than 15 nm and not more than 20000 nm is 0.04 to 0.15 $cm^3/g$, and a volume of pores with a diameter of not less than 1000 nm and not more than 20000 nm is 0.02 $cm^3/g$ or less, as measured by the mercury intrusion technique, and a tapped bulk density is 620 to 780 g/L.

2 Claims, 5 Drawing Sheets

(51) Int. Cl.

| | |
|---|---|
| ***B01J 35/00*** | (2024.01) |
| ***B01J 35/10*** | (2006.01) |
| ***B01J 35/61*** | (2024.01) |
| ***B01J 35/63*** | (2024.01) |
| ***B01J 35/64*** | (2024.01) |
| ***B01J 37/08*** | (2006.01) |
| *B01J 35/32* | (2024.01) |
| *B01J 35/40* | (2024.01) |
| *B01J 35/55* | (2024.01) |

(52) U.S. Cl.

CPC ............. *B01J 35/657* (2024.01); *B01J 37/08* (2013.01); *C07C 17/156* (2013.01); *B01J 35/32* (2024.01); *B01J 35/40* (2024.01); *B01J 35/55* (2024.01); *B01J 2235/00* (2024.01)

(56) References Cited

U.S. PATENT DOCUMENTS

| | | | | |
|---|---|---|---|---|
| 5,166,120 | A | 11/1992 | Deller et al. | |
| 7,807,604 | B2 * | 10/2010 | Strebelle | C07C 17/156<br>502/328 |
| 2010/0152505 | A1 * | 6/2010 | Orsenigo | B01J 27/122<br>423/625 |
| 2010/0160697 | A1 | 6/2010 | Orsenigo et al. | |
| 2019/0152795 | A1 * | 5/2019 | Kawakami | B01J 21/04 |
| 2021/0213423 | A1 * | 7/2021 | Schwab | B01J 21/04 |
| 2022/0410124 | A1 * | 12/2022 | Hernandez | B01J 21/04 |

FOREIGN PATENT DOCUMENTS

| | | | | |
|---|---|---|---|---|
| JP | 2001-226172 | A | 8/2001 | |
| JP | 2010-149115 | A | 7/2010 | |
| JP | 2012-187569 | A | 10/2012 | |
| JP | 2013-086070 | A | 5/2013 | |
| WO | WO-2021105252 | A1 * | 6/2021 | B01J 37/04 |
| WO | WO-2021105253 | A1 * | 6/2021 | B01J 37/038 |

* cited by examiner

ALUMINA SUPPORT

TECHNICAL FIELD

One or more embodiments of the present invention relate to an alumina support for a catalyst for a gas-phase reaction.

BACKGROUND

A support formed of an alumina compact has been widely used as a support for catalysts. Such an alumina support is composed of active alumina with the γ structure or a structure close thereto.

An alumina support is usually obtained by molding and calcining alumina hydrate (aluminum hydroxide) as a raw material. The molded compact may have a hollow columnar shape, because it provides a larger area of contact between a catalyst to be supported on the support and a material to be treated and causes a lower pressure loss during various operations. The molding method may be compression molding to ensure the strength of the support.

Patent Document 1 teaches a catalyst formed of a hollow columnar alumina compact made by compression molding. The catalyst has a cylindrical shape with an outer dimeter D of 3 mm to less than 6 mm, an inner diameter of not less than 1.0 mm, a thickness of not more than 1.5 mm, and a height H of 3 to 6 mm. This catalyst is particularly suitable as a fixed catalyst for an oxyhalogenation reaction or a halogenation reaction.

Meanwhile, compression molding usually leads to a lower specific surface area and a smaller pore volume. More specifically, when a high tableting pressure is set for compression molding, the resultant alumina compact will have increased strength, but at the same time there is a tendency to cause mesopores and macropores to shrink, as well as to reduce the specific surface area. Thus, the compact will suffer a drastic decrease in adsorption capability and activity.

In view of the above, the applicant provided an alumina-based compact made of alumina powder 50 to 95 weight % of which had the γ structure or a structure close thereto, the compact having a crushing strength per unit height of not less than 0.30 kg/mm, and a pore distribution peak at 90 to 150 angstroms in a pore diameter range of 20 to 700 angstroms, as measured by the nitrogen adsorption method (see Patent Document 2.) This alumina compact has high strength and high apparent density, maintains high levels of adsorptive properties and surface activity, and inhibits the shrinkage of mesopores serving as adsorption sites and macropores functioning as spaces for stably introducing a material to be catalytically treated to the mesopores.

As described in Patent Document 2 by the applicant, it has been conventionally recognized that inhibiting the shrinkage of mesopores and macropores is an effective way to exhibit catalytic activity. In particular, in order to effectively exhibit catalytic activity, it has been considered necessary to use an alumina support that holds a sufficient volume of macropores with a diameter of not less than 1000 nm.

PATENT DOCUMENTS

Patent Document 1: JP-A-56-141842

Patent Document 2: JP-A-2001-226172

The conventional alumina support with the controlled pore structure increases the catalytic activity, but at the same time also increases unintended and unnecessary activity like side reaction activity. As such, it has been demanded to provide an alumina support that is capable of both increasing the intended catalytic reaction activity and suppressing by-product formation.

Therefore, one or more embodiments of the present invention provide an alumina support for a catalyst for a gas-phase reaction that increases the catalytic reaction activity and allows a reduction in by-product yield especially when a chlorination catalyst such as a copper chloride catalyst is supported.

SUMMARY

One or more embodiments of the present invention provide an alumina support for a catalyst for a gas-phase reaction, having a tubular shape with at least one hollow through hole and a BET specific surface area of 140 to 280 $m^2/g$. A volume (total pore volume) of pores with a diameter of not less than 15 nm and not more than 20000 nm is 0.04 to 0.15 $cm^3/g$, and a volume of pores with a diameter of not less than 1000 nm and not more than 20000 nm is 0.02 $cm^3/g$ or less, as measured by the mercury intrusion technique. A tapped bulk density is 620 to 780 g/L.

The alumina support of one or more embodiments of the present invention may be as follows:

(1) The alumina support has an average pressure capacity of not less than 18 N;

(2) The alumina support has a cylindrical shape with one hollow hole that passes through the support in a height direction, an outer diameter of 3 to 6 nm, an inner diameter of not less than 1.0 mm, a thickness of 1.0 to 2.5 mm, and a height of 3 to 6 mm; and (3) The alumina support is used as a support for a catalyst for a gas-phase chlorination reaction of ethylene.

One or more embodiments of the present invention further provide a catalyst for a gas-phase reaction that is one or more metal compounds supported on the above-described alumina support.

In the catalyst for a gas-phase reaction of one or more embodiments of the present invention, the metal compounds may include copper chloride.

In the catalyst for a gas-phase reaction of one or more embodiments of the present invention, it is preferable that a volume of pores with a diameter of not less than 15 nm and not more than 20000 nm is 0.04 to 0.15 $cm^3/g$, and a volume of pores with a diameter of not less than 1000 nm and not more than 20000 nm is 0.02 $cm^3/g$ or less, as measured by the mercury intrusion technique.

The catalyst for a gas-phase reaction of one or more embodiments of the present invention may be used as a catalyst for producing dichloroethane by a gas-phase chlorination reaction of ethylene.

One or more embodiments of the present invention further provide a method for producing the above-described alumina support, including: using alumina hydrate having at least two particle size distribution peaks in a particle diameter region of not more than 300 μm; mixing the alumina hydrate with a fatty acid metal salt to prepare a molding raw material; compression molding the molding raw material into a tubular body with at least one hollow through hole; and calcining the tubular body to convert the alumina hydrate into alumina.

In the method for producing the alumina support of one or more embodiments of the present invention, the alumina hydrate may have a median diameter ($D_{50}$) of 45 to 100 μm, a diameter $D_{10}$ of 1 to 10 μm, and a diameter $D_{90}$ of 180 to 400 μm.

As used herein, the terms "mesopores" and "macropores" are used for illustration purpose in view of the relative diameter size of pores; mesopores refer to pores with a diameter of not less than 2 nm and less than 50 nm, and macropores refer to pores with a diameter of not less than 50 nm and not more than 20000 nm.

One or more embodiments of the present invention provide a method for producing dichloroethane, including using the catalyst for a gas-phase reaction of one or more embodiments of the present invention.

The method for producing dichloroethane of one or more embodiments of the present invention may include reacting ethylene with a hydrogen chloride gas and oxygen at 220° C. to 330° C. in the presence of the catalyst of the present invention.

One or more embodiments of the present invention provide a method for producing a vinyl chloride monomer, including thermally decomposing the aforementioned dichloroethane.

A particularly important feature of the alumina support of one or more embodiments of the present invention is that it has a pore structure with a lower ratio of macropores such that the total pore volume is 0.04 to 0.15 $cm^3/g$, and the volume of pores with a diameter of not less than 1000 nm and not more than 20000 nm is 0.02 $cm^3/g$ or less, as measured by the mercury intrusion technique.

One or more embodiments of the present invention have proved that the alumina support with the aforementioned pore structure increases the catalytic reaction activity and allows a reduction in by-product yield. This finding has been obtained through phenomena observed in repeated experiments; however, the reason has yet to be identified. In particular, this finding runs counter to the previous perception that an alumina support needs to hold a sufficient volume of macropores with a diameter of not less than 1000 nm for effective catalytic activity. In order to increase the catalytic reaction activity and to reduce the by-product yield, it is necessary to achieve both high catalytic activity and easy release of reaction heat. This is attributed to the idea that a by-product is formed by reaction heat. Presumably, it is contemplated that the above-described pore structure highly achieves both high catalytic activity and easy release of reaction heat.

The catalyst for a gas-phase reaction of one or more embodiments of the present invention is characterized by high catalytic activity and very high selectivity for dichloroethane (EDC) despite its high pressure capacity.

DETAILED DESCRIPTION

<Alumina Support>

Figure 1:
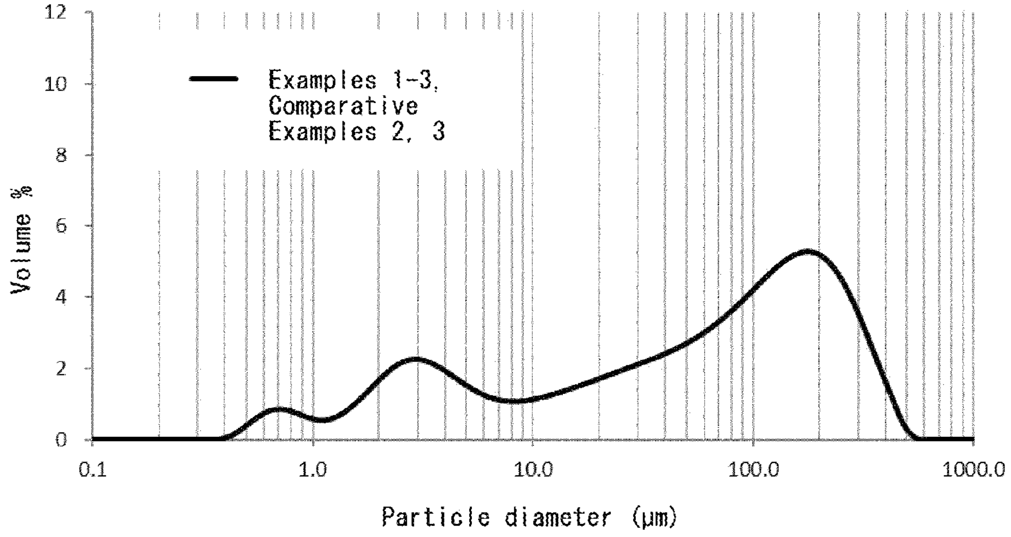
FIG. 1 is a graph showing the particle size distribution as obtained by the laser diffraction/scattering method for an alumina hydrate raw material used in each of Examples 1 to 3 and Comparative Examples 2 and 3.

An alumina support of one or more embodiments of the present invention is not particularly limited as to its crystal structure as long as it has a multi-pore structure as described below. The alumina support may have the γ, θ, δ, η or κ crystal structure, but is suitably made of γ-alumina because it makes it possible to easily form a particularly stable multi-pore structure.

In the present disclosure, the total pore volume refers to the volume of pores with a diameter of not less than 15 nm and not more than 20000 nm.

The alumina support of one or more embodiments of the present invention has a multi-pore structure with mesopores and macropores.

The total pore volume of the alumina support of one or more embodiments of the present invention may be 0.04 to 0.15 $cm^3/g$, or 0.06 to 0.11 $cm^3/g$.

If the total pore volume is less than 0.04 $cm^3/g$, it may be difficult to form certain amounts of mesopores and macropores. If the total pore volume is more than 0.15 $cm^3/g$, the performance of the alumina support for supporting a catalytically active component may decline such that the heat resistance and compression strength of the alumina support are reduced. As a result, the alumina support may not be able to maintain a stable pore structure due to heat contraction, degradation and the like, possibly resulting in difficulty in ensuring stable catalytic performance.

In the alumina support of one or more embodiments of the present invention, the volume of macropores of not less than 1000 nm and not more than 20000 nm may be 0.02 $cm^3/g$ or less, 0.01 $cm^3/g$ or less, or 0.008 $cm^3/g$ or less, provided that the total pore volume falls within the aforementioned range. If the alumina support of one or more embodiments of the present invention has a higher macropore volume, the by-product yield tends to increase, while the catalytic reaction activity is also increased. Thus, if the macropore volume is more than 0.02 $cm^3/g$, by-product formation may not be sufficiently reduced.

In one or more embodiments of the present invention, the total pore volume and the macropore volume as described above are measured by the mercury intrusion technique.

Further, in relation to the total pore volume and the volume of macropores of not less than 1000 nm and not more than 20000 nm falling within the above-described ranges, the alumina support of one or more embodiments of the present invention may have a high specific surface area, namely a BET specific surface area of 140 to 280 $m^2/g$, or 160 to 260 $m^2/g$, as measured by the nitrogen adsorption method.

In the alumina support of one or more embodiments of the present invention, the tapped bulk density may be 620 to 780 g/L, or 650 to 750 g/L. The tapped bulk density is obtained from the volume and weight of the alumina support when a receptacle such as a reactor or a cylinder containing the alumina support is tapped. The tapped bulk density increases with an increase in pressure during compression molding. It also varies according to calcination conditions.

If the tapped bulk density is less than 620 g/L, the compression strength and the abrasion strength decrease as compared with the case where the tapped bulk density falls within the aforementioned range. If the tapped bulk density is more than 780 g/L, the pore volume decreases with the increased density, possibly resulting in a decrease in catalytic reaction activity.

As shown in a graph, the Log differential pore volume distribution of the alumina support of one or more embodiments of the present invention, which is obtained from the pore volume as measured by the mercury intrusion technique, may have a peak within a range of 100 to 1100 nm, or within a range of 300 to 1000 nm, in a pore diameter region of not less than 50 nm. If a peak is not located within this range, there is a possibility of reducing the catalytic reaction activity and increasing the by-product yield.

In the graph, the Log differential pore volume distribution of the alumina support of one or more embodiments of the present invention may have no peak in a pore diameter region of 15 to 50 nm. If a peak is present in this region, there is a possibility of reducing the catalytic reaction activity and increasing the by-product yield.

As shown in a graph, the differential pore volume distribution of the alumina support of one or more embodiments of the present invention, which is obtained from the pore volume as measured by the nitrogen adsorption method, may have a peak within a range of 3 to 9 nm, or within a range of 4 to 7 nm. If a peak is not located within this range, there is a possibility of reducing the catalytic reaction activity and increasing the by-product yield.

The alumina support of one or more embodiments of the present invention may have an average pressure capacity of not less than 18 N, or not less than 20 N. In the present disclosure, the pressure capacity refers to a load applied from the vertically upward direction to the alumina support put on its side until the support is crushed, and the average pressure capacity refers to an average of capacities measured for arbitrarily selected 20 alumina supports.

When the average pressure capacity of the alumna support is not less than 18 N, a catalyst obtained from the alumina support of one or more embodiments of the present invention has an average pressure capacity equal to or more than that of the alumina support.

The alumina support of one or more embodiments of the present invention has a cylindrical shape with a single hollow hole that passes through the support in the height direction. The hollow cylindrical shape allows the compact to have high pressure capacity, provides a larger area of contact between the compact and a reactant or a material to be treated, and causes a lower pressure loss during various operations.

From the viewpoint of ensuring the pressure capacity and the contact area and causing a lower pressure loss as mentioned above, the cylindrical shape may have an outer diameter of 3 to 6 mm, particularly 4 to 5.5 mm; an inner diameter of not less than 1.0 mm, particularly not less than 1.5 mm; a thickness of 1.0 to 2.5 mm, particularly 1.0 to 2.0 mm; a height of 3 to 6 mm, particularly 4 to 5.5 mm; and a ratio of the inner diameter to the outer diameter of 0.17 to 0.67, particularly 0.27 to 0.64.

Further, the alumina support of one or more embodiments of the present invention may assume a conventionally known tubular shape depending on the intended use. The preferable shape is not particularly limited as long as the alumina support has at least one hollow hole that passes through the support in the height direction as disclosed in JP-A-2017-154051, for example.

The alumina support of one or more embodiments of the present invention may contain, as an impurity, $Fe_2O_3$ derived from an alumina hydrate raw material. The content of $Fe_2O_3$ is suitably not more than 400 ppm, more suitably not more than 200 ppm, in order not to inhibit the activity of a catalyst to be supported and not to increase by-product formation. Further, the alumina support of one or more embodiments of the present invention can contain a certain amount of metal component derived from a fatty acid metal salt as a raw material. The content of the metal component can be appropriately adjusted depending on the intended use according to the type and amount of a fatty acid metal salt to be used. In general, the metal component is an oxide of alkali metal or alkali earth metal. When the alumina support of one or more embodiments of the present invention is used as a support for a catalyst for a gas-phase chlorination reaction of ethylene, the metal component may be an alkali earth metal oxide. The content of the metal component derived from a fatty acid metal salt may fall within a range of 0.01 to 5 weight % of the alumina support of one or more embodiments of the present invention.

The alumina support of one or more embodiments of the present invention, which is for a catalyst for a gas-phase reaction, may be used for a catalyst for a gas-phase chlorination reaction of ethylene.

There are two patterns in the gas-phase chlorination reaction of ethylene as follows: the oxychlorination reaction in which ethylene is reacted with hydrogen chloride and oxygen; and the direct chlorination reaction in which ethylene is reacted directly with chlorine. A catalyst on the support of one or more embodiments of the present invention is available for both of the reaction patterns. The catalyst may be used for the oxychlorination reaction of ethylene.

<Catalyst for Gas-Phase Reaction>

A catalyst for a gas-phase reaction of one or more embodiments of the present invention is any one or more metal compounds supported as a catalytic component on the alumina support of one or more embodiments of the present invention. The catalyst for a gas-phase reaction of one or more embodiments of the present invention is highly activated and gives a lower by-product yield during a catalytic reaction because of the significantly characteristic pore distribution of the alumina support of one or more embodiments of the present invention.

The metal compound as a catalytic component can be supported on the alumina support by a known method, such as an impregnation method in which the alumina support of one or more embodiments of the present invention is immersed in and filled with a solution of a soluble salt as a catalytic active component. The impregnation method may be used because it is easily handled and advantageous in stably maintaining the catalyst properties. For example, it is preferable that the alumina support of one or more embodiments of the present invention is immersed in an impregnation solution at ordinary temperature or higher and kept under conditions that allow the support to be sufficiently impregnated with a desired component. The concentration, amount and temperature of the impregnation solution can be adjusted appropriately so that a desired amount of the catalytic component is supported.

The catalyst for a gas-phase reaction, which is the metal compound supported as described above, is appropriately loaded into a reactor or the like for use.

The metal compound to be supported can contain copper, vanadium, manganese, chromium, molybdenum, tungsten, iron, cobalt, nickel, osmium, platinum, palladium, rhodium, iridium, ruthenium or the like.

Among them, a copper compound, particularly copper chloride, or most suitably copper (II) chloride may be supported so as to be highly activated and kept with high stability, when the catalyst for a gas-phase reaction of one or more embodiments of the present invention is used for a gas-phase oxychlorination reaction of ethylene.

Moreover, when the catalyst further contains one or two metal compounds of Group I elements of the periodic table (e.g., potassium chloride, cesium chloride, etc.) in addition to copper chloride, it is possible to reduce by-product formation or, in other words, to improve the selectivity for dichloroethane (EDC).

The copper chloride-supported catalyst of one or more embodiments of the present invention may be used for a gas-phase oxychlorination reaction of ethylene.

A gas-phase oxychlorination reaction of ethylene produces dichloroethane (hereinafter, referred to as "EDC"; structure: Cl—$CH_2$—$CH_2$—Cl) by the chlorination of ethylene. At this time, monochloroethane (hereinafter, referred to as "EtCl"; structure: $CH_3$—$CH_2$—Cl) is produced as a by-product.

A catalyst for ethylene oxychlorination is required to have suitable catalytic activity for a reactor and high selectivity for EDC. If the catalyst has too high activity, the selectivity for EDC usually tends to decrease.

The catalytic activity of the copper chloride-supported catalyst for a gas-phase oxychlorination reaction of ethylene may be not less than 6.0 g-EDC ($cm^3$-catalyst•Hr), or not less than 7.0 g-EDC ($cm^3$-catalyst•Hr).

The catalytic activity can be controlled by controlling the concentration of copper chloride and the total pore (15 to 20000 nm) volume. The concentration of copper chloride may be in a range of 10.0 to 18.0 weight %. The total pore (15 to 20000 nm) volume may be in a range of 0.05 to 0.200 $cm^3/g$.

The relative selectivity of monochloroethane as a main by-product (hereinafter, referred to as "by-product selectivity") is evaluated by the ratio (EtCl/EDC) of production of monochloroethane to that of EDC, which may be not more than 0.4, or not more than 0.35.

The ratio of production of monochloroethane as a by-product is desirably lower, because a lower ratio eventually leads to higher selectivity for EDC.

The by-product selectivity can be controlled by controlling the concentration of the additional metal salt, such as potassium chloride, and the macropore (1000 to 20000 nm) volume. The concentration of the additional metal salt like potassium chloride may be in a range of 1.0 to 7.0 weight %. The macropore (1000 to 20000 nm) volume may be in a range of 0.001 to 0.02 $cm^3/g$.

The reaction system for producing EDC by an oxychlorination reaction is not particularly limited, and any reaction system is available. Examples include a fixed-bed flow system and a fluidized-bed flow system. In particular, a fixed-bed flow system may be used, because it uses a simple device.

The oxychlorination catalyst of one or more embodiments of the present invention is characterized by very high selectivity for EDC despite its high pressure capacity.

The fixed-bed oxychlorination catalyst may have a hollow cylindrical shape from the viewpoint of not only causing a lower pressure loss as described above regarding the alumina support, but also improving the selectivity for EDC.

Since a gas-phase oxychlorination reaction of ethylene is an exothermal reaction, heat buildup in a catalyst tends to lead to increased formation of by-product other than EDC. In order to avoid this, a catalyst body may have a lower height; however, a catalyst with a too low height will be cracked or pulverized. In view of these, the catalyst may have a small thickness while having a hollow cylindrical shape to maintain pressure capacity.

The oxychlorination catalyst of one or more embodiments of the present invention may have an average pressure capacity of not less than 18 N, or not less than 20 N. A catalyst with a pressure capacity of not less than 18 N is seldom broken or pulverized when loaded into a reactor, and is less likely to be broken or pulverized while being operated in the reactor.

It is desirable for the catalyst to have such properties that it is less likely to be broken or pulverized in a reactor, so as to suppress a differential pressure rise in the reactor.

<Method for Producing Alumina Support>

A method for producing the alumina support of one or more embodiments of the present invention is characterized by the following steps: preparing alumina hydrate having at least two particle size distribution peaks in a particle diameter region of not more than 300 μm; mixing the alumina hydrate with a fatty acid metal salt to prepare a molding raw material; compression molding the molding raw material into a tubular body having at least one hollow through hole; and calcining the tubular body to convert the alumina hydrate (aluminum hydroxide) into alumina (aluminum oxide).

The alumina hydrate has at least two particle size distribution peaks in a particle diameter region of not more than 300 μm. The alumina hydrate may have three or more particle size distribution peaks in a particle diameter region of not more than 300 μm.

The particle size distribution peaks may be present in two or more ranges among a range of not less than 0.1 μm and less than 1.0 μm, a range of not less than 1.0 μm and not more than 10.0 μm, and a range of not less than 100 μm and not more than 300 μm. It is particularly preferable that at least one particle size distribution peak is present in each of the three ranges.

It is advantageous in forming a multi-pore structure that the alumina hydrate for use in the production of the alumina support of one or more embodiments of the present invention has at least two particle size distribution peaks as described above. Besides, the broader each peak width, the higher the catalytic reaction activity and the lower the by-product yield.

The alumina hydrate may be pseudoboehmite, because alumina, preferably alumina with the γ structure or a structure close thereto, produced through pseudoboehmite calcination has a high BET specific surface area of 140 to 280 $m^2/g$, for example.

The alumina hydrate may be in the form of a powder for convenience in loading of the alumina hydrate into a molding machine. Such a powder may have a median diameter ($D_{50}$ of 45 to 100 μm, a diameter $D_{10}$ of 1 to 10 μm, and a diameter $D_{90}$ of 180 to 400 μm. If the median diameter ($D_{50}$ and the diameters $D_{10}$ and $D_{90}$ of the powder do not fall within these ranges, the pore distribution specific to the alumina support of one or more embodiments of the present invention may not be achieved.

The alumina hydrate may have a water content of not more than 20 weight %, or not more than 15 weight %. If the water content is more than 20 weight %, a crack is liable to be formed during the calcination.

The fatty acid metal salt as a raw material for the alumina compact of one or more embodiments of the present invention is blended for the purpose of, for example, reducing friction during the compression molding and forming pores in the alumina support by volatilizing the fatty acid metal salt during the calcination.

Examples of the fatty acid metal salt include magnesium stearate, calcium stearate, sodium stearate, and potassium stearate. Among them, magnesium stearate is preferred in one or more embodiments of the present invention.

The fatty acid metal salt may be added in an amount of 2 to 7 weight %, or in an amount of 3 to 6.5 weight %, with respect to the alumina hydrate as a raw material.

If the addition amount of the fatty acid metal salt is less than 2 weight %, the alumina hydrate may stick to a compression molding machine, possibly resulting in significantly reduced productivity. If the addition amount of the fatty acid metal salt is more than 7 weight %, macropores of not less than 1000 nm and not more than 20000 are increased, so that by-product formation may not be sufficiently reduced.

The raw material for the alumina compact of one or more embodiments of the present invention may contain, if needed, an inorganic diluent or binder in the form of a powder in an amount of not more than 50 weight %, or in an amount of 2 to 10 weight %, with respect to the alumina hydrate. Examples of the diluent or binder include a clay mineral of the kaolin group such as kaolin, halloysite, kibushi clay, or gairome clay; a clay mineral of the montmorillonite group such as montmorillonite, bentonite, or beidelite; and a trioctahedral clay mineral such as saponite, stevensite, or hectorite.

According to one or more embodiments of the present invention, the above-described raw materials are mixed together to prepare a molding raw material. The mixture is compression molded and thermally treated, thereby providing an alumina compact. The raw materials can be mixed with a mixing machine known per se, such as a conical blender, a ribbon blender, or a Henschel mixer.

For the compression molding, a known molding machine is used. In general, a molding machine includes a mold with a pestle for forming a hollow through hole, e.g., a mortar (tubular mold) combined with an upper pestle (piston for applying pressure to a raw material from above the mortar) and a lower pestle (piston for applying pressure to the raw material from below the mortar). With such a molding machine, the compression molding is performed by the following steps:

(1) loading a raw material powder into the mortar while the upper pestle is highly placed and the lower pestle is lowly placed;
(2) compressing the raw material powder in the mortar by the upper pestle moving downward or further by the lower pestle moving upward;
(3) releasing a compact compressed in the mortar from the mortar by moving the upper pestle and the lower pestle upward; and
(4) returning to prepare for loading with the lower pestle moved downward.

In Step (1), air may be supplied to facilitate the loading of the raw material powder into the motor.

Powder behavior during compression molding is as follows: Voids of a powder and granular material gradually decrease, allowing particles to adhere tightly to one another to form a compact. This process is considered to be divided into the following four stages:

First stage, in which raw material particles slide on one another to fill voids and become denser;

Second stage, in which when a higher pressure is applied, a bridge of powder is broken to fill voids, and the raw material itself is also deformed;

Third stage, in which the particles are partially crushed and new surfaces are exposed, so that the particles are tightly bonded together; and Fourth stage, in which the raw material particles are work hardened to the limit, until there is no further change in volume even by application of pressure, after which molding is terminated.

Actually, these four stages are not clearly distinguished, and some of them may occur simultaneously. The raw material mixture (molding raw material) for use in one or more embodiments of the present invention, which is the mixture of alumina hydrate and a fatty acid metal salt as described above, has excellent compression moldability and allows a uniform compact to be formed with a high yield.

The raw material mixture (molding raw material) for use in one or more embodiments of the present invention can be molded by a single-stroke compression molding machine but may be molded by a continuous or rotary compression molding machine. For example, such a continuous or rotary compression molding machine includes a number of compression molding units, each having the combination of the mortar with the upper and lower pestles as described above, which are arranged around a rotating turret. As the turret is rotated, Steps (1) to (4) are sequentially carried out, after which the compression molding is completed.

The shape and size of the tubular body (compact) with a hollow through hole to be obtained by the compression molding can be freely selected by changing the shape and size of the pestle or mold. In a case where the hollow hole passing through the tubular body in the height direction is provided at one location, it may be located to pass through the center of the tubular body from the viewpoint of strength. In a case where the hollow holes are provided at two or more locations, they are located at appropriate positions adjusted to achieve desirable compression strength and abrasion strength according to the intended use.

In the production of the alumina support of one or more embodiments of the present invention, it is preferable to adjust the compact density during the compression molding so as to control the pore structure of the alumina support. The compact density during the compression molding is adjusted by the amount of raw material to be loaded, the compression strength and the like. In the case of using a continuous or rotary compression molding machine, the compact density is usually evaluated based on the weight of the compact per height. More specifically, since the outer diameter and the inner diameter are fixed by the size of the mold, the mass of the compact per height can be used as a simple index. Considering that the mass of the compact varies with the amount of water adherent to the raw material, it is preferable to obtain the water amount in advance, so that the compact density can be managed based on the reduced dry mass of the compact at 150° C.

The thus-evaluated compact density during the compression molding may be 0.016 to 0.024 g/mm, or 0.018 to 0.022 g/mm. If the compact density during the compression molding is less than 0.016 g/mm, the compression strength and the abrasion strength may decrease. If the compact density during the compression molding is more than 0.024 g/mm, the pore volume and the specific surface area may decrease, possibly resulting in a decrease in catalytic activity.

According to one or more embodiments of the present invention, the thus-obtained tubular body (compact) with a hollow through hole is finally calcined to provide an alumina support. The calcination temperature may be 450° C. to 750° C., or 500° C. to 700° C. It is appropriate to perform a thermal treatment at the aforementioned temperature for approximately 30 minutes to 5 hours. If the calcination temperature is less than 450° C., the resultant alumina support may not have sufficient pressure capacity. If the calcination temperature is more than 750° C., the pore distribution specific to the alumina support of one or more embodiments of the present invention may not be achieved.

<Method for Producing Dichloroethane Using Gas-Phase Reaction Catalyst>

According to a method for producing dichloroethane using the oxychlorination catalyst of one or more embodiments of the present invention, ethylene, hydrogen chloride and oxygen as raw materials are reacted under controlled conditions at a suitable temperature and pressure. Oxygen can be replaced by air or oxygenated air.

The reaction temperature is not particularly limited, but may be 100° C. to 400° C., or 150° C. to 350° C., for efficient conversion to EDC. The reaction temperature may be 200° C. to 330° C.

The reaction pressure is not particularly limited. Usually, the absolute pressure may be 0.01 to 2 MPa, or 0.05 to 1 MPa.

Further, the gas hourly space velocity (GHSV) during a fixed-bed flow reaction may be 1,000 to 10,000 $hr^{-1}$, or 2,000 to 8,000 $hr^{-1}$, in order for the EDC production reaction to proceed efficiently. As used herein, the gas hourly space velocity (GHSV) refers to the value obtained by dividing the total gas supply amount ($m^3$/h) by the catalyst loading amount ($m^3$). This numerical value represents the performance of the loaded catalyst in terms of the reaction amount.

The catalytic performance is desirably such that a sufficient reaction amount can be ensured even at high GHSV.

Dichloroethane produced by the method for producing dichloroethane using the oxychlorination catalyst of one or more embodiments of the present invention is further thermally decomposed, thereby providing a vinyl chloride monomer.

EXAMPLES

One or more embodiments of the present invention will be described by way of Examples below, though one or more embodiments of the present invention are not limited to these Examples.

The following experiments were performed using various measuring methods described below.

(1) Particle Size Measurement of Raw Material

Mastersizer 3000 and Hydro LV manufactured by Malvern Panalytical Ltd were used for measurement by the laser diffraction/scattering method. Water was used as a dispersion medium. An analysis was made at a refractive index of 1.68 and a dispersion medium refractive index of 1.33 based on the Mie theory of light scattering.

(2) Specific Surface Area and Differential Pore Volume Distribution

TriStar II 3020 manufactured by Micromeritics Instrument Corporation was used for measurement by the nitrogen adsorption method. The specific surface area was analyzed from the adsorption branch of the nitrogen adsorption isotherm at a relative pressure of not less than 0.05 and not more than 0.20 at −196° C. by using the BET method. The differential pore volume distribution was obtained through analysis from the desorption branch of the nitrogen adsorption isotherm by using the BJH method.

(3) Pore Volume

AutoPore IV 9500 manufactured by Micromeritics Instrument Corporation was used for measurement by the mercury intrusion technique. A sample with a weight of about 1.5 g was measured under a room temperature atmosphere at a pressure in a range of not less than 10 psia and not more than 15000 psia, thereby measuring the volume of pores of not less than 15 nm and not more than 20000 nm. The cumulative intrusion volume at a pressure in the aforementioned range was regarded as the total pore volume, and the cumulative intrusion volume at a pressure of not less than 10 psia and not more than 220 psia was obtained as the volume of macropores having a diameter of not less than 1000 nm and not more than 20000 nm.

(4) Log Differential Pore Volume Distribution

AutoPore IV 9500 manufactured by Micromeritics Instrument Corporation was used for measurement by the mercury intrusion technique. A sample with a weight of about 0.5 g was measured at a pressure in a range of not less than 10 psia and not more than 60000 psia, thereby obtaining the Log differential pore volume distribution for not less than 3.6 nm and not more than 20000 nm.

(5) Pressure Capacity

Desktop load tester 1310D manufactured by Aikoh Engineering Co., Ltd. and a 50 N load cell were used to measure the strength of the alumina support in a direction perpendicular to the lateral side of the alumina support tube. The measurement was made on 20 alumina supports. A load was applied from the lateral side of the tube at a loading speed of 5 mm/min, and a load applied when the alumina support was destroyed was digitally displayed for reading. The average value of the 20 measurements was regarded as the pressure capacity.

(6) Tapped Bulk Density

A sample of 200 g was poured into a 500 $cm^3$ measuring cylinder and then tapped until there was no further change in the volume occupied. A volume reading was taken, and the packed density was calculated.

(7) Preparation of Catalyst for Gas Phase Oxychlorination Reaction of Ethylene 9.76 g of copper (II) chloride dihydrate, 1.94 g of potassium chloride, and 1.94 g of cesium chloride were dissolved in 25 $cm^3$ of pure water to prepare a solution, in which the hollow cylindrical alumina support of 50 g was immersed at room temperature for 30 minutes. The immersed alumina support was taken out and dried in an electric furnace at a temperature of 200° C. for two hours. Thereafter, the alumina support was calcined at 350° C. for two hours to provide a catalyst.

It was confirmed that the metal compounds were supported in the thus-obtained catalyst in the following amounts: 12 weight % of copper (II) chloride, 3 weight % of potassium chloride, and 3 weight % of cesium chloride. The catalyst was the same size as the alumina support.

The quantities of the metal compounds were determined in the following manner: 3 g of the oxychlorination catalyst was ground with a mill and boiled and dissolved in concentrated hydrochloric acid, followed by diluting to 100 $cm^3$ with distilled water to prepare a sample solution. The sample solution was sprayed on a flame atomic absorption spectrophotometer (product name: AA-7000, manufactured by Shimadzu Corporation), thereby determining the quantities of the metal components. From the determined quantities of the metal components, the amounts of the supported metal compounds with respect to the catalyst weight were calculated.

(8) Activity Evaluation

For dichloroethane (EDC) production, a reaction test was performed using a fixed-bed flow reactor including a small cylindrical reaction tube of nickel (inner diameter: 26 mm), in which 3 g of the obtained catalyst and inactive glass beads were contained as a catalytic packed bed with a height of about 19 cm.

During the reaction, the reaction temperature inside the reactor was maintained at approximately 220° C. to 270° C. by keeping the temperature of an outer jacket, which uses silicone oil as a heat transfer medium, set and controlled at 240° C.

A raw material gas was introduced from the top of the reactor and passed through the catalytic bed to be reacted, after which the reacted gas was discharged to the outside from the bottom of the reactor. At this time, the outlet gauge pressure of the reactor was controlled at 0.4 MPaG.

As the raw material gas, a hydrogen chloride gas, ethylene, and air were allowed to flow at rates of 150 NL/Hr, 81 NL/Hr, and 80.3 NL/Hr, respectively. The unit NL as used herein represents the volume L (0.001 $m^3$) in normal conditions (0° C., 1 atm).

The gas discharged from the reactor was condensed in 2,2,4-trimethylpentane cooled in two stages at −38° C. and −45° C. and then recovered.

The amount of EDC produced was obtained by measuring the EDC concentration in the condensate by a gas chromatograph. The amount of monochloroethane produced as a main by-product was obtained by measuring its concentration in the non-condensable gas by a gas chromatograph.

The analysis of the condensate was made by a gas chromatograph (model name: GC 14B, manufactured by Shimadzu Corporation), using as a filler SE 30 (product name) manufactured by GL Science Inc.

The analysis of the non-condensable gas was made by a gas chromatograph (model name: GC 14B, manufactured by Shimadzu Corporation), using as a filler Porapak Q (product name) manufactured by Waters Corporation.

The catalytic activity value was calculated from the amount of dichloroethane (EDC) produced from 1 g of the catalyst per hour. The by-product selectivity was evaluated by the ratio (EtCl/EDC) of the amount of monochloroethane produced to that of EDC.

Example 1

Alumina hydrate (pseudoboehmite) was prepared that had particle size distribution peaks at 0.7 μm, 2.9 μm and 174 μm as shown in FIG. 1, and a median diameter ($D_{50}$) of 67.7 μm, a diameter $D_{10}$ of 2.43 μm and a diameter $D_{90}$ of 258 μm. 10 kg of this alumina hydrate (pseudoboehmite) was mixed with 500 g of magnesium stearate to form a molding raw material. The molding raw material was loaded into a mold (mortar) with an outer diameter of 4.8 mm and an inner diameter of 2.2 mm, and then pressurized by upper and lower pestles, thereby providing a compression molded product having a compact density of 0.0201 g/mm in terms of the dry mass of the product at 150° C. This product was calcined at 620° C. for two hours to provide an alumina support with the γ crystal structure. The alumina support had a cylindrical shape with a single hollow hole that passes through the center of the circular support in the height direction. The circular support had an outer dimeter of 4.5 mm, an inner diameter of 2.0 mm, a thickness of 1.25 mm, and a height of 5.0 mm.

A catalyst for a chlorination reaction of ethylene prepared from the thus-obtained alumina support had an EDC activity of 7.65 g-EDC/($cm^3$-catalyst•Hr) and a by-product selectivity of 0.30.

Example 2

An alumina support was obtained by the same operation as in Example 1, except that a product had a compact density of 0.0208 g/mm in terms of the dry mass of the product at 150° C. The alumina support had a cylindrical shape with an outer dimeter of 4.5 mm, an inner diameter of 2.0 mm, a thickness of 1.25 mm, and a height of 5.0 mm as in Example 1.

A catalyst for a chlorination reaction of ethylene prepared from the thus-obtained alumina support had an EDC activity of 6.65 g-EDC/($cm^3$-catalyst•Hr) and a by-product selectivity of 0.31.

Example 3

An alumina support was obtained by the same operation as in Example 1, except that a product had a compact density of 0.0199 g/mm in terms of the dry mass of the product at 150° C. The alumina support had a cylindrical shape with an outer dimeter of 4.5 mm, an inner diameter of 2.0 mm, a thickness of 1.25 mm, and a height of 5.0 mm as in Example 1.

A catalyst for a chlorination reaction of ethylene prepared from the thus-obtained alumina support had an EDC activity of 7.13 g-EDC/($cm^3$-catalyst•Hr) and a by-product selectivity of 0.34.

Comparative Example 1

Figure 2:
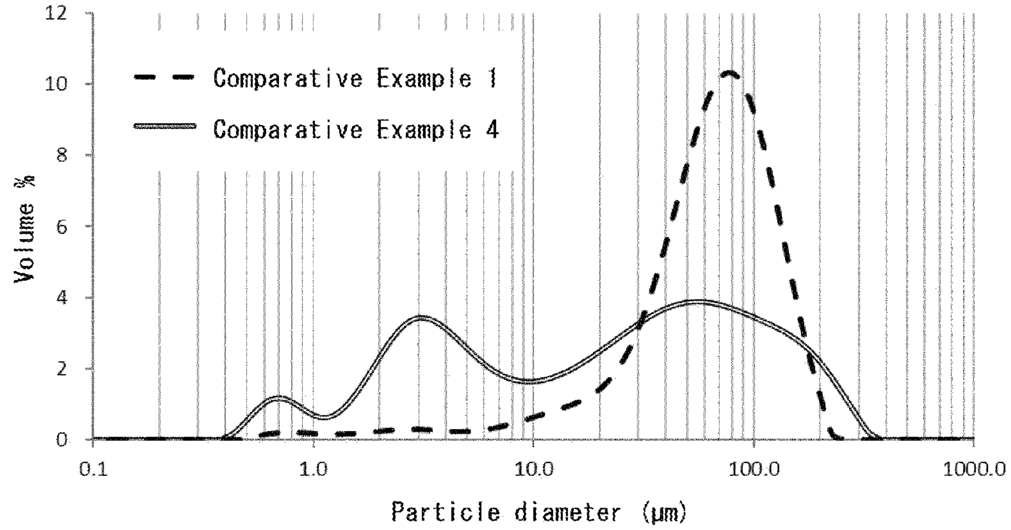
FIG. 2 is a graph showing the particle size distribution as obtained by the laser diffraction/scattering method for an alumina hydrate raw material used in each of Comparative Examples 1 and 4.
Figure 3:
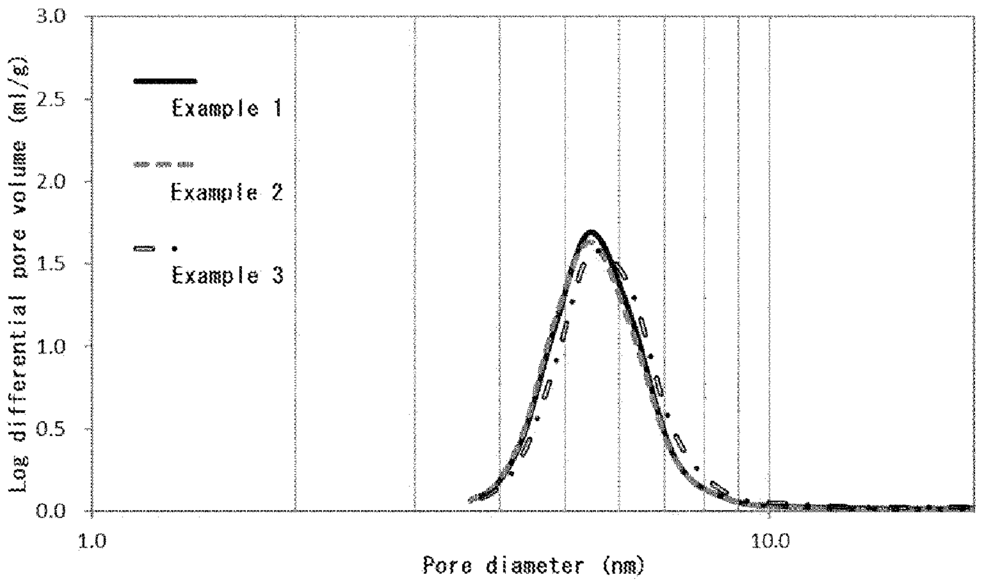
FIG. 3 is a graph showing the Log differential pore volume distribution as measured by the mercury intrusion technique over a pore diameter of 1.0 to 10.0 nm in each of Examples 1 to 3.
Figure 4:
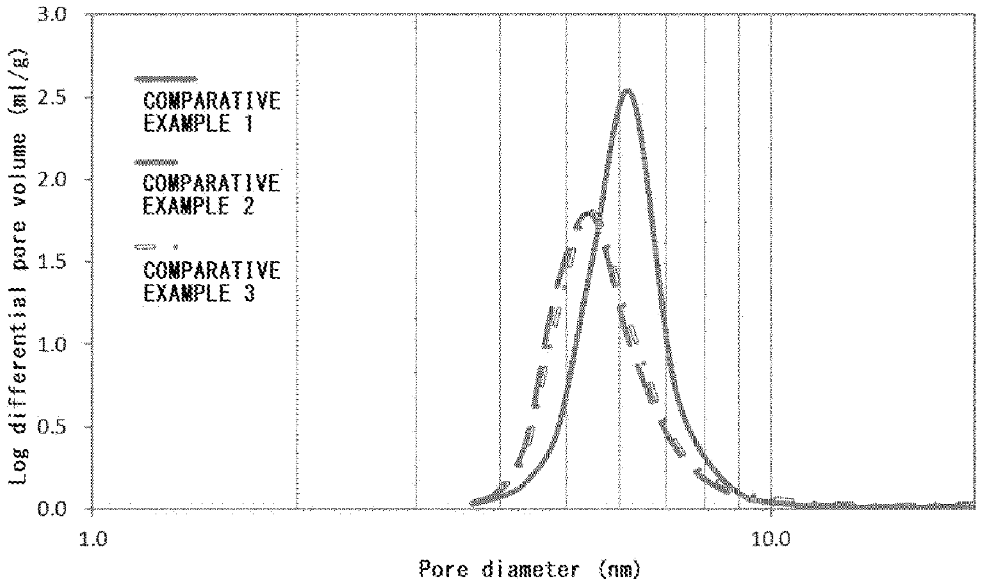
FIG. 4 is a graph showing the Log differential pore volume distribution as measured by the mercury intrusion technique over a pore diameter of 1.0 to 10.0 nm in each of Comparative Examples 1 to 3.
Figure 5:
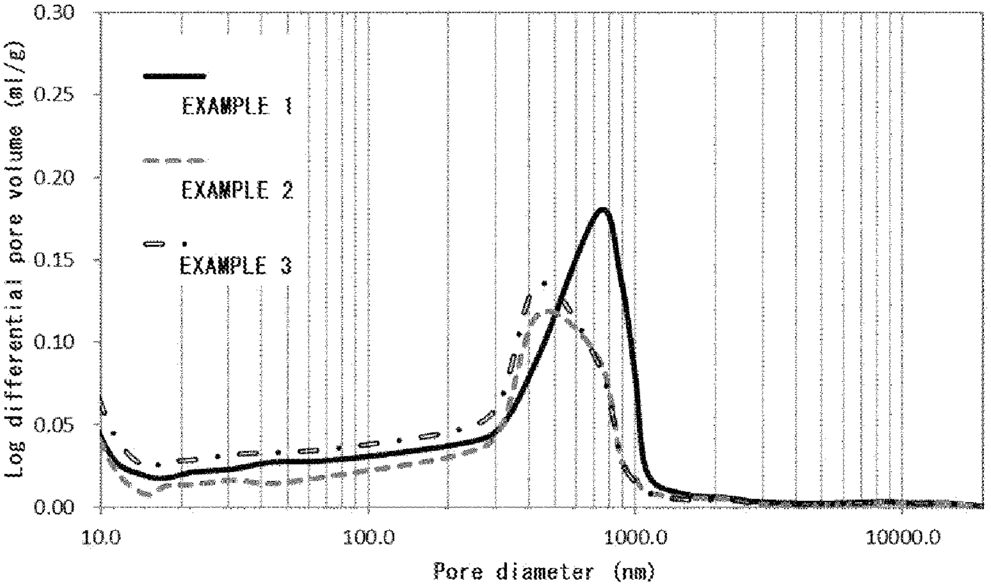
FIG. 5 is an enlarged view of a graph showing the Log differential pore volume distribution as measured by the mercury intrusion technique over a pore diameter of 10.0 to 10000.0 nm in each of Examples 1 to 3.
Figure 6:
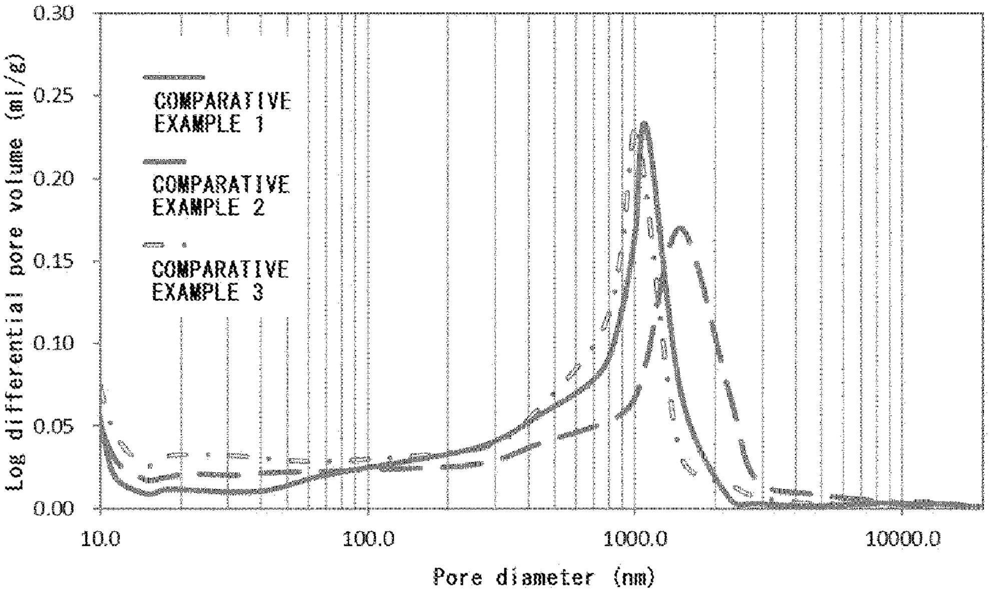
FIG. 6 is an enlarged view of a graph showing the Log differential pore volume distribution as measured by the mercury intrusion technique over a pore diameter of 10.0 to 10000.0 nm in each of Comparative Examples 1 to 3.
Figure 7:
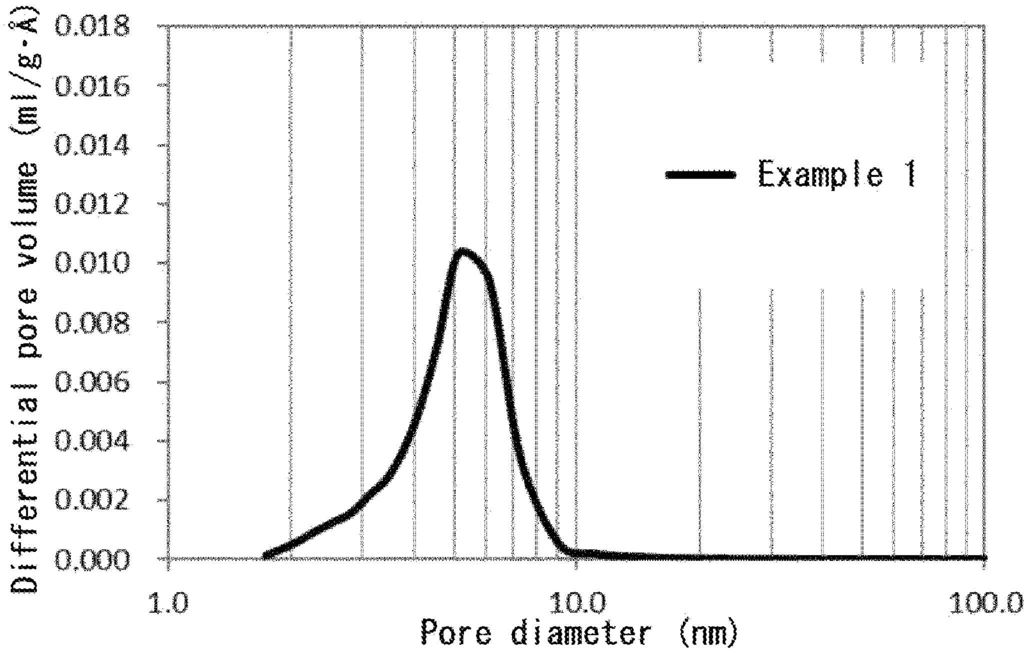
FIG. 7 is a graph showing the differential pore volume distribution as measured by the nitrogen adsorption-desorption BJH method in Example 1.
Figure 8:
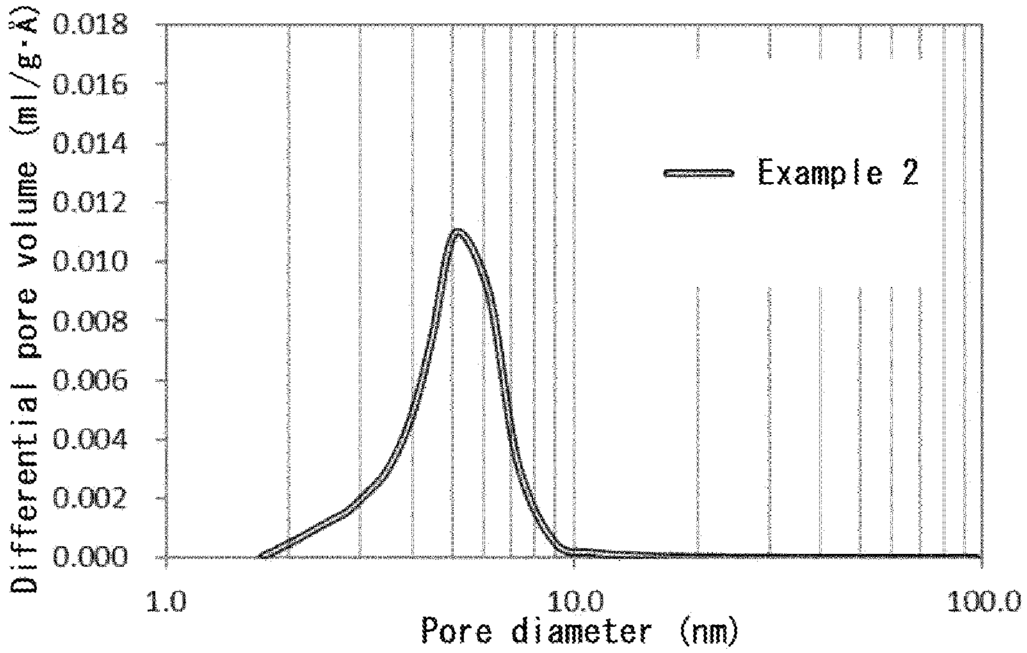
FIG. 8 is a graph showing the differential pore volume distribution as measured by the nitrogen adsorption-desorption BJH method in Example 2.
Figure 9:
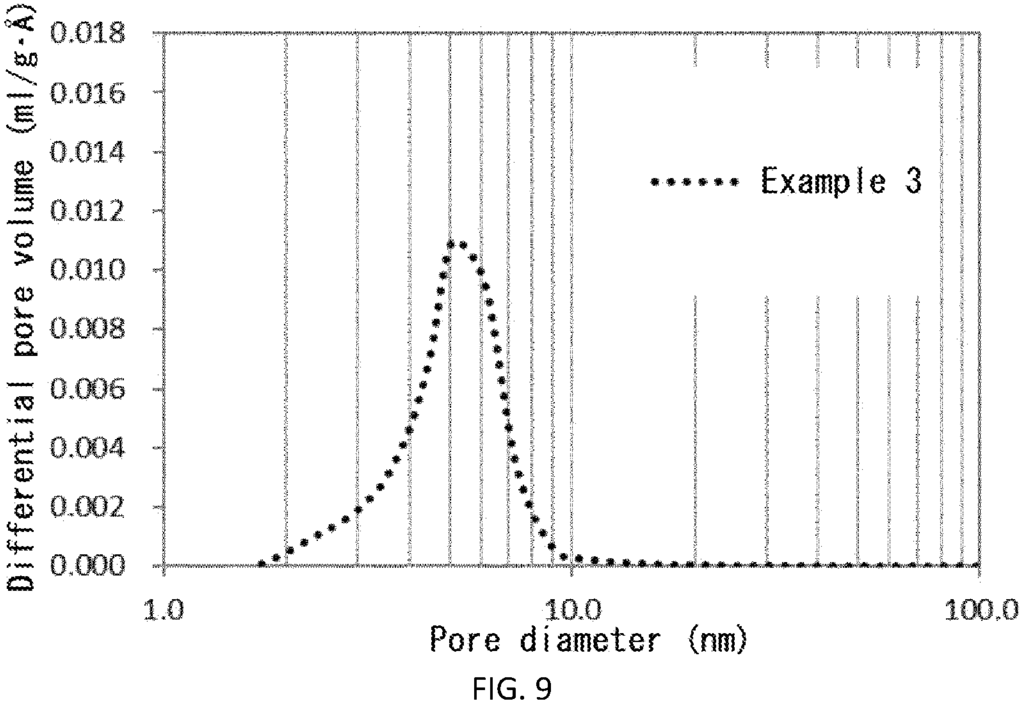
FIG. 9 is a graph showing the differential pore volume distribution as measured by the nitrogen adsorption-desorption BJH method in Example 3.
Figure 10:
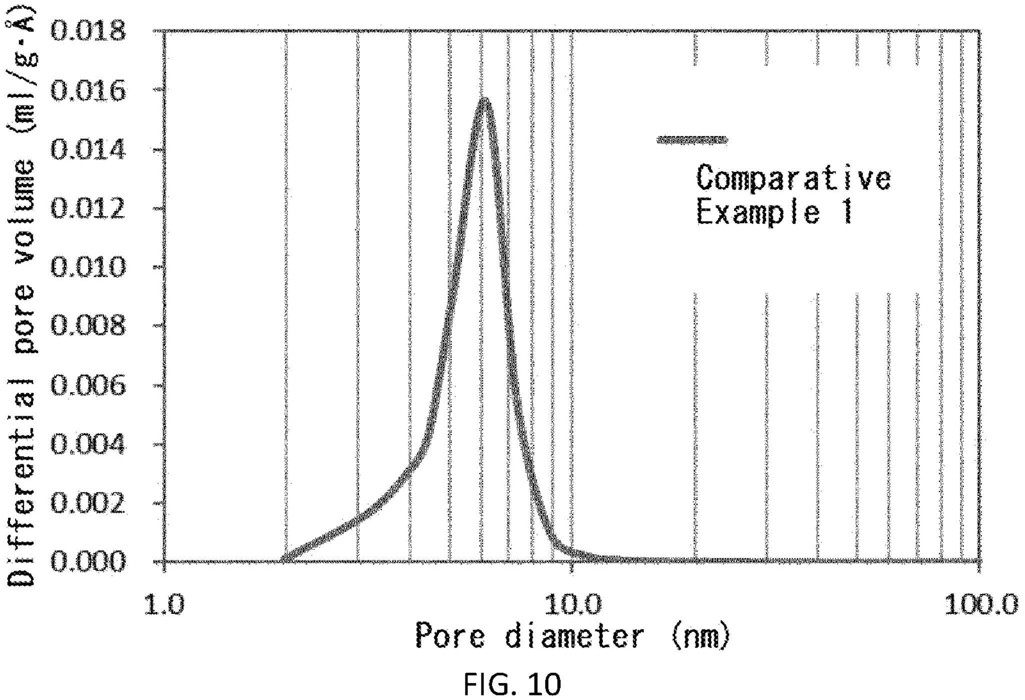
FIG. 10 is a graph showing the differential pore volume distribution as measured by the nitrogen adsorption-desorption BJH method in Comparative Example 1.

An alumina support with the γ crystal structure was obtained by the same operation as in Example 1, except that alumina hydrate (pseudoboehmite) was used that had only one particle size distribution peak at a particle diameter of 81 μm as shown in FIG. 2, and a median diameter ($D_{50}$) of 67.3 μm, a diameter $D_{10}$ of 21.9 μm and a diameter $D_{90}$ of 132 μm, and that a product had a compact density of 0.0200 g/mm in terms of the dry mass of the product at 150° C. The alumina support had a cylindrical shape as in Example 1 with an outer dimeter of 4.6 mm, an inner diameter of 2.0 mm, a thickness of 1.3 mm, and a height of 5.0 mm.

A catalyst for a chlorination reaction of ethylene prepared from the thus-obtained alumina support had an EDC activity of 7.84 g-EDC/($cm^3$-catalyst•Hr) and a by-product selectivity of 0.35.

Comparative Example 2

An alumina support was obtained by the same operation as in Example 1, except that 800 g of magnesium stearate was used, and that a product had a compact density of 0.0197 g/mm in terms of the dry mass of the product at 150° C. The alumina support had a cylindrical shape with an outer dimeter of 4.5 mm, an inner diameter of 2.0 mm, a thickness of 1.25 mm, and a height of 5.0 mm as in Example 1.

A catalyst for a chlorination reaction of ethylene prepared from the thus-obtained alumina support had an EDC activity of 7.03 g-EDC/($cm^3$-catalyst•Hr) and a by-product selectivity of 0.35.

Comparative Example 3

An alumina support was obtained by the same operation as in Comparative Example 2, except that a product had a compact density of 0.0196 g/mm in terms of the dry mass of the product at 150° C. The alumina support had a cylindrical shape with an outer dimeter of 4.5 mm, an inner diameter of 2.0 mm, a thickness of 1.25 mm, and a height of 5.0 mm as in Comparative Example 2.

A catalyst for a chlorination reaction of ethylene prepared from the thus-obtained alumina support had an EDC activity of 7.86 g-EDC/($cm^3$-catalyst•Hr) and a by-product selectivity of 0.42.

Comparative Example 4

An alumina support was obtained by the same operation as in Example 1, except that alumina hydrate (pseudoboehmite) was used that had particle size distribution peaks at particle diameters of 0.7 μm, 2.9 μm and 48.6 μm as shown in FIG. 2, and a median diameter ($D_{50}$) of 25.1 μm, a diameter $D_{10}$ of 2.02 μm and a diameter $D_{90}$ of 161 μm, and that a product had a compact density of 0.0151 g/mm in terms of the dry mass of the product at 150° C. The alumina support had a cylindrical shape as in Example 1 with an outer dimeter of 4.5 mm, an inner diameter of 2.0 mm, a thickness of 1.25 mm, and a height of 4.6 mm.

The samples obtained in Examples and Comparative Examples were evaluated for physical properties and catalytic performance; the results are shown in Table 1.

TABLE 1

| Test item | Unit | *Ex. 1 | Ex. 2 | Ex. 3 | **Compr. Ex. 1 | Compr. Ex. 2 | Compr. Ex. 3 | Compr. Ex. 4 |
|---|---|---|---|---|---|---|---|---|
| Median diameter (D50) | μm | 67.7 | 67.7 | 67.7 | 67.3 | 67.7 | 67.7 | 25.1 |
| D10% diameter | | 2.43 | 2.43 | 2.43 | 21.9 | 2.43 | 2.43 | 2.02 |
| D90% diameter | | 258 | 258 | 258 | 132 | 258 | 258 | 161 |
| Peak top in a region of | | 0.7 | 0.7 | 0.7 | 81 | 0.7 | 0.7 | 0.7 |
| not more than 300 μm | | 2.9 | 2.9 | 2.9 | | 2.9 | 2.9 | 2.9 |
| | | 174 | 174 | 174 | | 174 | 174 | 48.6 |
| Rate of adding fatty acid metal salt | mass % | 4.8 | 4.8 | 4.8 | 4.8 | 7.4 | 7.4 | 4.8 |
| Compact density in terms of dry mass at 150° C. | g/mm | 0.0201 | 0.0208 | 0.0199 | 0.0200 | 0.0197 | 0.0196 | 0.0151 |
| Specific surface area | $m^2/g$ | 194 | 197 | 203 | 207 | 208 | 199 | — |
| Volume of pores (total pores) of 15-20000 nm | $cm^3/g$ | 0.098 | 0.081 | 0.103 | 0.111 | 0.104 | 0.121 | 0.326 |
| Volume of pores (macropores) of 1000-20000 nm | $cm^3/g$ | 0.005 | 0.007 | 0.004 | 0.036 | 0.027 | 0.030 | 0.043 |
| Pressure capacity | N | 25.8 | 31.8 | 25.2 | 17.0 | 24.7 | 24.4 | 10.9 |
| Tapped bulk density | g/L | 669 | 699 | 678 | 642 | 667 | 656 | — |
| EDC activity | g-EDC/$cm^3$-catalyst•Hr | 7.65 | 6.65 | 7.13 | 7.84 | 7.03 | 7.86 | — |
| By-product selectivity | EtCl/EDC | 0.30 | 0.31 | 0.34 | 0.35 | 0.35 | 0.42 | — |

*Example;
**Comparative Example

Examples 1-3 and Comparative Examples 2 and 3 prove that a raw material having three particle size distribution peaks in a region of not more than 300 μm and a median diameter of 45 to 100 μm can be used to achieve an alumina support with a pressure capacity of more than 20 N. Further, Examples 1-3 prove that when the total pore volume is 0.04 to 0.15 $cm^3/g$, and the volume of macropores having a diameter of not less than 1000 nm and not more than 20000 nm is 0.02 $cm^3/g$ or less, a catalyst exhibits a high EDC activity of not less than 6.6 g-EDC/($cm^3$-catalyst•Hr) and high selectivity for EDC with a by-product selectivity of less than 0.35.

Although the disclosure has been described with respect to only a limited number of embodiments, those skilled in the art, having benefit of this disclosure, will appreciate that various other embodiments may be devised without departing from the scope of the present disclosure. Accordingly, the scope of the invention should be limited only by the attached claims.

The invention claimed is:

1. A method of producing dichloroethane comprising reacting ethylene with a hydrogen chloride gas and oxygen with a catalyst comprising one or more metal compounds supported on an alumina support which has a tubular shape with at least one hollow through hole; and a BET specific surface area of 140 to 280 $m^2/g$, wherein a volume of pores of the alumina support with a diameter of not less than 15 nm and not more than 20000 nm is 0.04 to 0.15 $cm^3/g$, and a volume of pores of the alumina support with a diameter of not less than 1000 nm and not more than 20000 nm is 0.02 $cm^3/g$ or less, as measured by mercury intrusion technique, and a tapped bulk density of the alumina support is 620 to 780 g/L.

2. A method of producing dichloroethane, comprising reacting ethylene with a hydrogen chloride gas and oxygen at 220° C. to 330° C. in the presence of a catalyst comprising one or more metal compounds supported on an alumina support which has a tubular shape with at least one hollow through hole; and a BET specific surface area of 140 to 280 $m^2/g$, wherein a volume of pores of the alumina support with a diameter of not less than 15 nm and not more than 20000 nm is 0.04 to 0.15 $cm^3/g$, and a volume of pores of the alumina support with a diameter of not less than 1000 nm and not more than 20000 nm is 0.02 $cm^3/g$ or less, as measured by mercury intrusion technique, and a tapped bulk density of the alumina support is 620 to 780 g/L.

* * * * *